United States Patent [19]

Babin et al.

[11] Patent Number: 5,420,159

[45] Date of Patent: May 30, 1995

[54] PYRETHRINOID ESTERS

[75] Inventors: Didier Babin, Montigny; Marc Benoit, Roquevaire; Jean-Pierre Demoute, Neuilly Plaisance, all of France

[73] Assignee: Roussel-Uclaf, France

[21] Appl. No.: 312,116

[22] Filed: Sep. 26, 1994

Related U.S. Application Data

[63] Continuation of Ser. No. 17,630, Feb. 12, 1993, abandoned.

[30] Foreign Application Priority Data

Feb. 21, 1992 [FR] France ............... 92 02010

[51] Int. Cl.$^6$ ............... A01N 53/00
[52] U.S. Cl. ............... 514/531; 549/66; 549/323; 558/257; 558/394; 558/398; 558/407; 560/8; 560/43; 560/55; 560/124
[58] Field of Search ............... 560/124; 514/531

[56] References Cited

U.S. PATENT DOCUMENTS

| | | | |
|---|---|---|---|
| 3,673,215 | 6/1972 | Vollrath | 560/124 |
| 3,792,079 | 2/1974 | D'Orazio | 560/124 |
| 4,024,163 | 5/1977 | Elliott | 560/124 |
| 4,252,820 | 2/1981 | Lantzsch | 560/124 |
| 4,310,540 | 1/1982 | Lantzsch | 560/124 |
| 4,332,815 | 6/1982 | Engel | 560/124 |
| 4,385,070 | 5/1983 | Bentley | 560/124 |
| 4,897,302 | 11/1989 | Tessier | 560/124 |
| 4,939,172 | 7/1990 | Cadiergue | 560/124 |
| 5,336,670 | 8/1994 | Beniot | 560/124 |

FOREIGN PATENT DOCUMENTS

| | | | |
|---|---|---|---|
| 61713 | 10/1982 | European Pat. Off. | 560/124 |
| 381563 | 8/1990 | European Pat. Off. | 560/124 |
| 3005722 | 8/1981 | Germany . | |
| 3900275 | 7/1990 | Germany . | |
| 58-121246 | 7/1983 | Japan | 560/124 |
| 2088369 | 6/1982 | United Kingdom | 560/124 |

Primary Examiner—Michael L. Shippen
Attorney, Agent, or Firm—Bierman and Muserlian

[57] ABSTRACT

All possible stereoisomeric forms and mixtures thereof of a compound of the formula

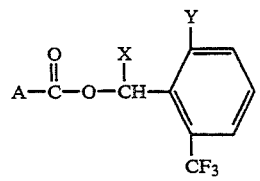

wherein X is selected from the group consisting of hydrogen, alkyl, alkenyl and alkynyl of up to 4 carbon atoms, —CN and aralkynyl of up to 10 carbon atoms, Y is selected from the group consisting of halogen, —CH$_2$F, —CHF$_2$, and —CF$_3$, A is selected from the group consisting of

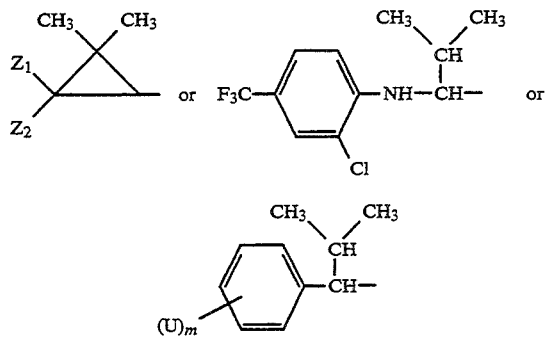

having pesticidal properties.

5 Claims, No Drawings

PYRETHRINOID ESTERS

This application is a continuation of U.S. patent application Ser. No. 017,630, filed Feb. 12, 1993, now abandoned.

Related prior art includes U.S. Pat. Nos. 3,792,079, 4,486,355, 4,808,749, 4,316,044, 4,277,494 and 4,405,639 and European application No. 0,181,284.

OBJECTS OF THE INVENTION

It is an object of the invention to provide the novel compounds of formula I and a novel process and intermediates for their preparation.

It is another objection of the invention to provide novel pesticidal compositions and a novel method of combatting pests.

These and other objects and advantages of the invention will become obvious from the following detailed description.

THE INVENTION

The novel compounds of the invention are all possible stereoisomeric forms and mixtures thereof of a compound of the formula

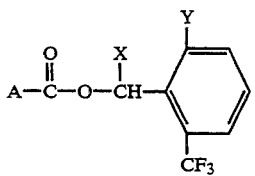

wherein X is selected from the group consisting of hydrogen, alkyl, alkenyl and alkynyl of up to 4 carbon atoms, —CN and aralkynyl of up to 10 carbon atoms, Y is selected from the group consisting of halogen, —CH$_2$F, —CHF$_2$, and —CF$_3$, A is selected from the group consisting

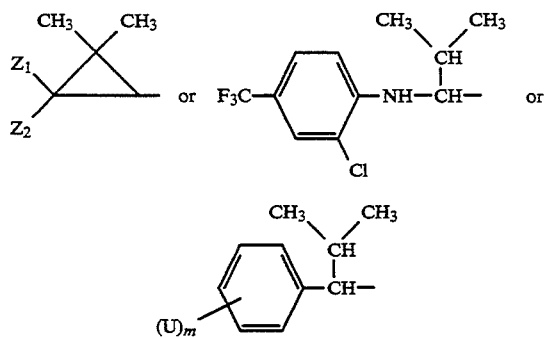

$Z_1$ and $Z_2$ are both methyl or $Z_1$, is hydrogen and $Z_2$ is selected from the group consisting of

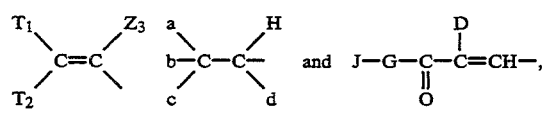

$Z_3$ is halogen or hydrogen, $T_1$ and $T_2$ are individually selected from the group consisting of hydrogen, halogen, alkyl and alkoxy of 1 to 8 carbon atoms optionally substituted by at least one halogen; mono-, di and trifluoromethyl, —CN and phenyl optionally substituted by halogen or $T_1$ and $T_2$ together with the carbon to which they are attached form a cycloalkyl of 3 to 6 carbon atoms or

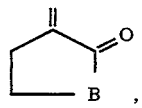

B is —O— or —S—, a, b, c and d are individually halogen, D is hydrogen or halogen or alkoxy of 1 to 8 carbon atoms, G is —O— or —S—, J is selected from the group consisting of alkyl and cycloalkyl of up to 8 carbon atoms optionally substituted with at least one functional group, aryl of 6 to 14 carbon atoms optionally substituted with at least one functional group and heterocycle optionally substituted with at least one functional group, U is in any position of the benzene and is selected from the group consisting of halogen and alkyl and alkoxy of 1 to 8 carbon atoms and m is 0, 1 or 2 and when m is 2, the U's may be different.

When X is alkyl, it is preferably methyl or ethyl and when X is alkenyl, it is preferably vinyl. When X is alkynyl, it is preferably ethynyl. When Y is halogen, it is preferably fluorine or chlorine or bromine. When $T_1$, $T_2$ or $Z_3$ is halogen, it is preferably fluorine, chlorine or bromine. When $T_l$ or $T_2$ is alkyl or alkoxy, it is preferably methyl, ethyl, propyl, methoxy, ethoxy or propoxy. a, b, c and d preferably are chlorine or bromine. When D is halogen, it is preferably fluorine, chlorine or bromine. When J is alkyl substituted by at least one functional group, alkyl is preferably of 1 to 8 carbon atoms such as, methyl, ethyl, propyl, isopropyl, butyl, isobutyl or tert-butyl and by functional group is meant one of those mentioned in the European Application under the 50534. J can also be alkyl substituted by aryl, particularly an optionally substituted phenyl. When J is alkyl substituted by at least one functional group, the group may be:

—(CH$_2$)$_{n1}$—C(Hal)$_3$ in which n1 is an integer from 1 to 8 and Hal is halogen, for example —CH$_2$—CCl$_3$, —CH$_2$—CF$_3$, —CH$_2$—CH$_2$—CCl$_3$ or CH$_2$—CH$_2$—CF$_3$;

—(CH$_2$)$_{n2}$—CH(Hal)$_2$ in which Hal is defined as above and n2 is a number from 0 to 8, for example —CH$_2$—CHCl$_2$, —CH$_2$—CHF$_2$ or —CHF$_2$;

—(CH$_2$)$_{n1}$—CH$_2$(Hal) in which n1 and Hal are defined as above for example —CH$_2$—CH$_2$Cl or —CH$_2$—CH$_2$F;

—C(Hal$_3$)$_3$ in which Hal is defined as above, for example the —C(CF$_3$)$_3$;

—C(CF$_3$)$_2$—CCl$_3$, —C(CF$_3$)$_2$—CH$_3$, —C(CH$_3$)$_2$—CF$_3$ or —C(CH$_3$)(CF$_3$)—CH$_2$—CH$_3$, —CH(CF$_3$)—CH$_3$ or —CH(CF$_3$)$_2$, —C(CH$_3$)$_2$—CN, —CH(CH$_3$)—CN or —(CH$_2$)$_n$—CN in which n is defined as previously, —CH(CN)—C(Hal)$_3$ in which Hal is defined as previously, for example:

—CH(CN)—CCl$_3$;

—(CH$_2$)$_{n1}$—OR$_a$, in which n1 is defined as previously and R$_a$ is hydrogen or alkyl of 1 to 8 carbon atoms, for example —CH$_2$—OCH$_3$, —CH$_2$—CH$_2$—O—CH$_3$, —CH$_2$—CH$_2$—O—CH$_2$—CH$_3$ or —CH$_2$—CH$_2$—OH;

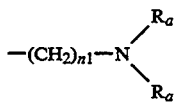

in which n1 and $R_a$ are defined as previously and the two $R_a$ can be different from each other, for example:
—$CH_2$—$CH_2$—NH—$CH_3$, —$CH_2$—$CH_2$—$N(CH_3)_2$ or —$CH_2$—$CH_2$—$N(CH_3)$—$CH_2$—$CH_3$;

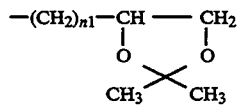

in which n1 is defined as previously, for example:

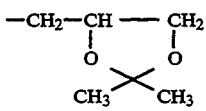

—$(CH_2)_{n1}$—CH(OH)—$CH_2$—OH in which n1 is defined as previously for example —$CH_2$—CH(OH)—$CH_2$—OH;

—$(CH_2)_{n1}$—O—THP in which n1 is defined as previously and THP is 2-tetrahydropyrannyl, for example:
—$CH_2$—O—THP or —$CH_2$—$CH_2$—O—THP;

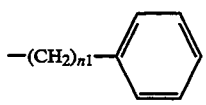

Among the preferred compounds of the invention, are those wherein Y is fluorine, those wherein Y— is $CF_3$, those wherein X is hydrogen, those wherein A, is

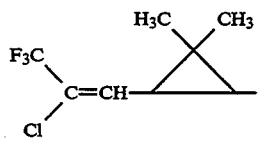

those wherein A is

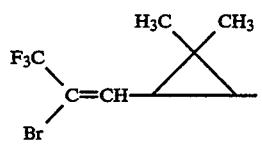

those wherein A is:

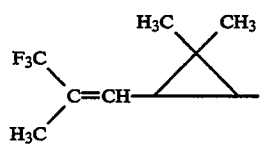

and those wherein A is the remainder of a cyclopropane acid of 1R cis structure.

The novel process of the invention for the preparation of the compounds of formula I comprises reacting an acid of the formula $$ACO_2H \qquad II$$

wherein A is defined as above, or a functional derivative of the acid with an alcohol of the formula

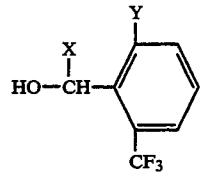

wherein X and Y have the above definitions or a functional derivative of the alcohol to obtain the corresponding compound of formula I.

The functional,derivative of the acid used is preferably an acid chloride. When the acid of formula II is reacted with the alcohol of formula III, the operation is preferably carried out in the presence of dicyclohexylcarbodiimide.

The acids of formula II used as starting products are generally known products used in the synthesis of pyrethrinoid compounds. Some acids are new and are an object of the invention as new industrial products.

The alcohols of formula III are known products and 2-fluoro 6-(trifluoromethyl) benzyl alcohol is a commercial product. 2,6-bis(trifluoromethyl) benzyl alcohol is a new product and is an object of the invention.

The novel pesticidal compositions of the invention are comprised of a pesticidally effective amount of at least one compound of formula I and an inert carrier. The compositions are useful for combatting parasites for example for combating parasites of vegetation, parasites of premises and parasites of warm-blooded animals and for combating parasitic insects, nematodes and acaridae of vegetation and of animals.

The compositions of the invention are for combating parasites of vegetation, parasites of premises and parasites of warm-blooded animals and can also be used for combating insects and other soil parasites, for example Coleoptera, such as Diabrotica, click beetles,and May beetle grubs, Myriapoda such as scutigeridae and blanjules, and Diptera such as cecydomia and Lepidoptera such as owlet moths. They are used at doses between 10 g and 300 g of active ingredient per hectare.

The compositions are useful also for combatting household insects such as houseflies, mosquitoes and cockroaches.

The products of formula I are photostable and are not very toxic for mammals, all of these properties mean that the products of formula I correspond perfectly to the requirements of the modern agrochemical industry: they enable crops to be protected while preserving the environment.

The compositions can also be used for combating parasitic acaridae and nematodes of vegetation as well as combating parasitic acaridae of animals, for combating for example ticks and in particularly ticks of Boophilus type, those of Hyalomnia type, those of Amblyomnia type and those of Rhipicephalus type, or for combating all types of mites and in particular the sarcoptic mite, the psoroptic mite and the chorioptic mite.

The compositions intended for combating parasites of warm-blooded animals, parasites of premises and of vegetation are characterized in that they contain at least one of the products of formula I and particularly, the products of Examples 1, 2, 3, 5 and 6.

The insecticide compositions contain at least one of the Products of formula I as active ingredient and may be prepared according to the usual processes of the agrochemical industry or the veterinary industry or the industry for products intended for animal fodder.

In the compositions intended for agricultural use and use in premises, one or more other pesticide agents can optionally be added to the active ingredient or ingredients. These compositions can be in the form of powders, granules, suspensions, emulsions, solutions, aerosol solutions, combustible bands, baits or other preparations usually employed for the use of these types of compounds.

In addition to the active ingredient, these compositions contain generally a vehicle and/or a non-ionic surfactant, to ensure a uniform dispersion of the components of the mixture. The vehicle used can be a liquid such as water, alcohol, hydrocarbons or other organic solvents, a mineral, animal or vegetable oil, a powder such as talc, clays, silicates, kieselguhr or a combustible solid.

The insecticide compositions according to the invention preferably contain 0.005% to 10% by weight of active ingredient. In an advantageous operating method for use in premises, the compositions of the invention are used in the form of fumigant compositions. The compositions according to the invention can advantageously be constituted, for the non-active part, by a combustible insecticide coil, or an incombustible fibrous substrate. In the latter case, the fumigant obtained after incorporation of the active ingredient is placed on a heating apparatus such as an electric emanator.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder. The dose of active ingredient can then be, for example, 0.03 to 1% by weight. In the case where an incombustible fibrous support is used, the dose of active ingredient can then be, for example, 0.03 to 95% by weight.

The compositions of the invention for use in premises can also be obtained by preparing a sprayable oil based on the active ingredient, this oil soaking the wick of a lamp and then being set alight. The concentration of active ingredient incorporated in the oil is, preferably, 0.03 to 95% by weight.

The insecticide compositions of the invention as acaricide and nematocide compositions can optionally have added to them one or more other pesticide agents. The acaricide and nematocide compositions can be presented in the form of powders, granules, suspensions, emulsions or solutions.

For acaricide use, wettable powders for foliar spraying, with 1 to 80% by weight of active ingredient or liquids for foliar spraying with 1 to 500 g/l of active ingredient are preferably used. Powders can also be used for foliar dusting containing 0.05 to 3% of active ingredient. For nematocide use, liquids are preferably used for soil treatment with 300 to 500 g/l of active ingredient. The acaricide and nematocide compositions of the invention are used, preferably, at doses between 1 and 100 g of active ingredient per hectare.

To enhance the biological activity of the products of the invention, they can contain standard synergists such as 1-(2,5,8-trioxadodecyl) 2-propyl 4,5-methylenedioxy benzene (or piperonyl butoxide) or N-(2-ethyl heptyl) bicyclo[2,2-1]5-heptene-2,3-dicarboximide, or piperonyl-bis-2-(2'-n-butoxy ethoxy) ethylacetal (or tropital).

The compounds of formula I have an excellent general tolerance, and therefore are useful for combating in particular illnesses caused by ticks and mites in man and in animals. The products of the invention are in particular used for combating lice in a preventative or curative way and for combating scabies.

The products of the invention can be administered externally by spraying, by shampooing, by bathing or by painting on. The products of the invention for veterinary use can also be administered by painting on the dorsal spine by the so-called "pour-on" method.

It can also be indicated that the products of the invention can be used as biocides or as growth regulators.

The compositions may also contain at least one of the pyrethrinoid esters selected from the group consisting of the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3-phenoxybenzyl alcohol and of alpha-cyano-3-phenoxybenzyl alcohol with 2,2-dimethyl-3-(2,2-dichlorovinyl)-cyclopropanecarboxylic acids, by the esters of alpha-cyano-3-phenoxy-benzyl alcohol with 2,2-dimethyl-3-(2,2-dibromovinyl)-cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of alpha-cyano-3-phenoxybenzyl alcohol with 2,2-dimethyl-3-(1,2,2,2-tetrahaloethyl)-cyclopropanecarboxylic acids, in which "halo" represents a fluorine, chlorine or bromine atom, it, being understood that the compounds of formula I can exist in all their possible stereoisomer forms, as well as the acid and alcohol copulas of the above pyrethrinoid esters.

The novel method of the invention for combatting insects comprises contacting insects with an insecticidally effective amount of at least one compound of formula I.

In the following examples, there are described several preferred embodiments to illustrate the invention. However, it is to be understood that the invention is not intended to be limited to the specific embodiments.

EXAMPLE 1

2,6-bis(trifluoromethyl) benzyl [1R,(1α,3α)] 3-[(Z) 2-chloro 3,3,3-trifluoro 1-propenyl] 2,2-dimethyl cyclopropane carboxylate A solution of 0.31 g of dicyclohexylcarbodiimide and 1.2 ml of methylene chloride was added at 0° C. to a mixture of 0.37 g of [1R,(1α, 3α)] 3-[(Z) 2-chloro 3,3,3-trifluoro 1-propenyl] 2,2-dimethyl cyclopropanecarboxylic acid, 5 ml of methylene chloride, 0.37 g of 2,6-bis(trifluoromethyl) benzyl alcohol the preparation of which is given hereafter and 4 mg of 4-dimethylamino pyridine. The reaction mixture was stirred for 3 hours and filtration was carried out. The filtrate was washed and evaporated to dryness under reduced pressure. The product was chromatographed on silica (eluant: hexane-ethyl acetate 95-5) to obtain 0.61 g of the desired product.

| NMR: CDCl$_3$ - 300 MHz | |
|---|---|
| H of the twinned methyls | 1.27 (s) and 1.29 (s) ppm |
| H in position 1 and 3 of the cyclopropane | 1.95 (d) J = 8.5 Hz and 2.16 (m) ppm |
| H of the CO$_2$ CH$_2$— | 5.28 (d) and 5.46 (d) ppm |
| ethylenic H | 6.90 (dd) ppm J = 9.5 and 1 Hz |
| aromatic H's | 7.66 (t) ppm, 7.97 (d) |

EXAMPLE 2

2-fluoro 6-trifluoromethyl benzyl [1R, (1α,3α)] 3-[(Z) 2-chloro 3,3,3-trifluoro 1-propenyl] 2,2-dimethyl cyclopropane carboxylate Using the procedure of Example 1, 4.18 g of [1R, (1α,3α)] 3-[(Z)2-chloro 3,3,3 -trifluoro 1-propenyl] 2,2 -dimethyl cyclopropanecarboxylic acid and 1 g of commercial 2-fluoro 6-trifluoromethyl benzyl alcohol were reacted to obtain 5.59 g of the desired product.

| NMR: CDCl$_3$ - 250 MHz | |
|---|---|
| H of the twinned methyls | 1.27 (s) and 1.29 (s) ppm |
| H in position 1 and 3 of the cyclopropane | 1.97 (d) J = 8.5 Hz and 2.16 (m) ppm |
| H of the CO$_2$ CH$_2$ | 5.30 [AB] |
| ethylenic H | 6.89 (d) ppm |
| aromatic H's | 7.33 (m) and 7.53 (m) ppm |

Using the procedure of Examples 1 and 2, the corresponding acids and alcohols were reacted to obtain the following products:

EXAMPLE 3

[2,6-bis-trifluoromethyl benzyl [1R(1α, 3α)] 3-[(Z)-2-bromo 3,3,3-trifluoro 1-propenyl] 2,2-dimethyl cyclopropane carboxylate

| NMR: CDCl$_3$ - 250 MHz | |
|---|---|
| H of the twinned methyls | 1.27 and 1.30 ppm |
| H in position 1 and 3 of the cyclopropane | 1.35 (d) J = 8.,5 Hz and 2.12 (m) ppm |
| H of the CO$_2$ CH$_2$ | 5.28 (d) J = 13 |
| ethylenic H Δ Z | 7.12 (d) ppm |

EXAMPLE 4

2-fluoro 6-trifluoromethyl benzyl [1R(1α, 3α)] 3-[(Z)-2-bromo 3,3,3-trifluoro 1-propenyl] 2,2-dimethyl cyclopropane carboxylate

| NMR: CDCl$_3$ - 250 MHz | |
|---|---|
| H of the twinned methyls | 1.28 (s) and 1.29 (s) ppm |
| H in position 1 and 3 of the cyclopropane | 1.28 (d) J = 8.5 Hz and 2.11 (m) ppm |
| H of the CO$_2$ CH$_2$ | 5.30 ppm |

EXAMPLE 5

2,6-bis trifluoromethyl benzyl [1R(1α, 3α)] 3-[(Z)-2-methyl 3,3,3-trifluoro 1-propenyl] 2,2-dimethyl cyclopropane carboxylate

| NMR: CDCl$_3$ - 250 MHz | |
|---|---|
| H of the twinned methyls | 1.27 (s) and 1.23 (s) ppm |
| CH$_3$—C= | 1.83 (s) ppm |
| H in position 1 and 3 of the cyclopropane | 1.85 (m) ppm |
| H of the CO$_2$ CH$_2$ | 5.26 (d) and 5.44 (d) ppm |

EXAMPLE 6

2-fluoro 6-trifluoromethyl benzyl [1R(1α, 3α)] 3-[(Z)-2-methyl 3,3,3-trifluoro 1-propenyl] 2,2-dimethyl cyclopropane carboxylate

| NMR: CDCl$_3$ - 250 MHz | |
|---|---|
| H of the twinned methyls | 1.24 (s) and 1.27 (s) ppm |
| CH$_3$—C= | 1.83 (s) ppm |
| H in position 1 and 3 of the cyclopropane | 1.85 (m) ppm |
| H of the CO$_2$ CH$_2$ | 5.28 ppm |

PREPARATION 1

2,6-bis-trifluoromethyl benzyl alcohol

STAGE A: methyl 2,6-bis(trifluoromethyl) benzoate

A solution of 6 g of 2,6-bis(trifluoromethyl) benzoic acid, 60 ml of tetrahydrofuran and 11.58 ml of a 2N sodium hydroxide solution was stirred for 30 minutes at 20° C. and after the solution was cooled to 0° C., 4.26 ml of dimethyl sulfate were added The mixture was stirred for one hour at 20° C. and another 2.1 ml of dimethyl sulfate were added. The reaction mixture was stirred for 24 hours at 20° C. and then poured into an aqueous solution of sodium bicarbonate. Extraction was carried out with isopropyl ether then with ethyl acetate. The extracts were dried, filtered, rinsed and evaporated to dryness to obtain after chromatography on silica (eluant: hexane-ethyl acetate (9-1)), 5.59 g of the desired product.

STAGE B: 2,6-bis-trifluoromethyl benzyl alcohol 58 ml of a 1.2M solution of diisobutylaluminium hydride (DIBAH) were added at 0° C. to a solution of 5.59 g of the product of Stage A and 60 ml of toluene. The temperature was allowed to return to 20° C. and the reaction mixture was stirred for 4 hours and then poured into a molar solution of potassium and sodium double tartrate. Extraction was carried out with isopropyl ether, and the aqueous phase was saturated with sodium chloride, followed by extraction with ethyl acetate. The extracts were dried, filtered, rinsed and evaporated to dryness to obtain after chromatography on silica (eluant: hexane-ethyl acetate (9-1)) , 4.72 g of the desired product.

PREPARATION 2

1R(1α, 3α)] 3-[(Z)-2-bromo 3,3,3-trifluoro 1-propenyl] 2,2-dimethyl cyclopropane carboxylic acid 1 g of methyl [1R (1α, 3α)] 2,2-dimethyl 3-(2,2-dibromoethenyl) cyclopropane carboxylate, 0.57 ml of trimethyl trifluoromethylsilane and 0.22 g of potassium fluoride in 10 ml of dimethylformamide were heated for one hour at 45° C. in the presence of 0.79 g of copper iodide. The same quantity of reagents was added again, and the mixture was stirred for 16 hours and then at 50° C., poured into an ice-cooled aqueous solution of sodium acid phosphate. Extraction was carried out with ether and the solvent was eliminated to obtain 1.3 g of crude expected product. Chromatography on silica (eluant: hexane-methylene chloride 8-2) yielded 250 mg of pure product.

PREPARATION 3

[1R(1α, 3α)] 2,2-dimethyl 3-[(Z)-2-methyl 3,3,3-trifluoro 1-propenyl] cyclopropane carboxylic acid

STAGE A: methyl 3-(2 -oxopropyl) 2,2-dimethyl cyclopropane carboxylate 10 g of 3-(2-oxopropyl) 2,2-dimethyl cyclopropane carboxylic acid in 100 ml of acetone were heated at 30° C. to 34° C. in the presence of 7.35 g of potassium bicarbonate and 5 ml of dimethylsulfate. After 4 hours of stirring, 0.85 ml of dimethylsulfate were added and the mixture was maintained for 20 hours at 30° to 34° C. After filtration, the filtrate was taken up in ethyl ether and the solvent was evaporated. The residue was chromatographed on silica (eluant: hexane-ethyl acetate 8-2) to obtain 10.43 g of the expected product is obtained.

STAGE B: methyl 3-(2-methyl 2-trimethylsilyloxy 3,3,3-trifluoropropyl) 2,2-dimethyl cyclopropane carboxylate 0.5 ml of terbutylammonium fluoride were added at 0° C. to 5 g of the product of Stage A and 8 ml of trifluoromethyl trimethylsilane in 65 ml of tetrahydrofuran, and the mixture was stirred for 15 minutes. The mixture was poured into an ice-cooled aqueous solution of potassium acid phosphate and extraction was carried out with ethyl ether. The extracts were dried and the solvent was evaporated to obtain 7.57 g of the expected product.

STAGE C: methyl 3-(2-methyl 2-hydroxy-3,3,3-trifluoropropyl) 2,2-dimethyl cyclopropane carboxylate 444 mg of potassium fluoride were added at ambient temperature to 500 mg of the product of Stage B in 5 ml of methanol and the mixture was stirred for 3 hours, poured into 25 ml of an aqueous solution of potassium acid phosphate. Extraction was carried out with ethyl ether, the extracts were dried and the solvent was evaporated to obtain 360 mg of the expected product.

STAGE D: methyl 2,2-dimethyl 3-[(Z) 2-methyl-3,3,3-trifluoro 1-propenyl]-cyclopropane carboxylate 22.3 ml of phosphorous oxychloride were added at 20° C. to 24.35 g of methyl 2,2-dimethyl 3-(2-methyl 2-hydroxy 3,3,3-trifluoropropyl) cyclopropane carboxylate of Stage C in 146 ml of pyridine. The mixture was heated at 74° C. for 6 hours and 30 minutes, left for 6 hours at ambient temperature and then poured into ice-cooled water. Extraction was carried out with isopropyl ether and the organic phase was washed with 2N hydrocloric acid, then with water, dried, and the solvent was evaporated. After chromatography on silica (eluant: hexane-ethyl acetate 75-25), 19.13 g of the expected product were obtained.

STAGE E: [1R(1α, 3α)] 2,2-dimethyl 3-[(Z)-2-methyl 3,3,3-trifluoro 1-propenyl] cyclopropane carboxylic acid 4.14 g of the product of Stage A in 52.6 ml of methanol were heated at 60° C. for 2 hours and 30 minutes in the presence of 19.3 ml of N sodium hydroxide and then for 30 minutes in the presence of an additional 2 ml of N sodium hydroxide. The reaction medium was poured into ice-cooled water, and extraction was carried out with isopropyl ether. The extracts were dried and the solvent was evaporated under reduced pressure to obtain 2.94 g of the expected product.

EXAMPLE 7

Preparation of a Soluble Concentrate

A homogeneous mixture was made of:

| | |
|---|---|
| Product of Example 1: | 0.25 g |
| Piperonyl butoxide: | 1.00 g |
| Tween 80: | 0.25 g |
| Topanol A: | 0.1 g |
| Water: | 98.4 g |

EXAMPLE 8

Preparation of an Emulsifiable Concentrate

The following were intimately mixed:

| | |
|---|---|
| Product of Example 2: | 0.015 g |
| Piperonyl butoxide: | 0.5 g |
| Topanol A: | 0.1 g |
| Tween 80: | 3.5 g |
| Xylene: | 95.885 g |

EXAMPLE 9

Preparation of an Emulsifiable Concentrate

A homogeneous mixture was made of:

| | |
|---|---|
| Product of Example 3: | 0.25 g |
| Piperonyl butoxide: | 1.00 g |
| Tween 80: | 0.25 g |
| Topanol A: | 0.1 g |
| Water: | 98.4 g |

EXAMPLE 10

Preparation of an Emulsifiable Concentrate

The following were intimately mixed:

| | |
|---|---|
| Product of Example 5: | 0.015 g |
| Piperonyl butoxide: | 0.5 g |
| Topanol A: | 0.1 g |
| Tween 80: | 3.5 g |
| Xylene: | 95.885 g |

EXAMPLE 11

Preparation of an Emulsifiable Concentrate

A homogeneous mixture was made of:

| | |
|---|---|
| Product of Example 6: | 1.5 g |
| Tween 80: | 20.00 g |

| | |
|---|---|
| -continued | |
| Topanol A: | 0.1 g |
| Water: | 78.4 g |

EXAMPLE 12

Preparation of Granules

Granules were prepared containing 0.1% to 5% of active substances.

BIOLOGICAL STUDY

A—Activity on Diabrotica

The test insects were last-stage larvae of Diabrotica and a 9 cm diameter disc of filter paper, placed at the bottom of a Petri dish, was treated with 2 ml of an acetonic solution of the product to be tested. After drying, 15 larvae per dose were deposited and the mortality check was carried out 24 hours after treatment. From a dose of 1 ppm, the products of the invention showed a good activity.

B—Study of the Knock-down Effect on a Housefly

The test insects were 4-day old female houseflies and the operation was carried out by spraying in a Kearns and March chamber using a mixture of acetone (5%) and Isopar L (petroleum solvent) as solvent (quantity of solvent used was 2 ml over one second). 50 insects were used per treatment and checks were carried out every minute up to 10 minutes, then after 15 minutes. The KT 50 was determined by the usual methods and at a dose of 1 g/l, the product of Example 2 showed a good activity.

C—Study of the Lethal Effect on a Housefly

The test insects were 4- to 5-day old female houseflies and the operation was carried out by topical application of 1 microliter of acetonic solution of the product to be tested on the dorsal thorax of the insect using an Arnold micro-manipulator. 50 individuals were used per treatment and mortality checks are carried out twenty-four hours after treatment. At a dose of 10 mg/l, the product of Example 2 showed a good activity.

Various modifications of the products and the method of the invention may be made without departing from the spirit or scope thereof and it is to be understood that the invention is intended to be limited only as defined in the appended claims.

What we claim is:

1. A stereoisomeric form or a mixture thereof of a compound of the formula

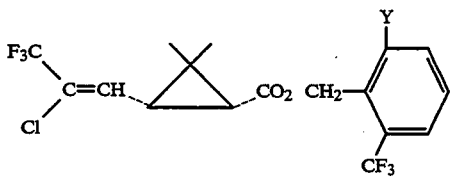

wherein Y is selected from the group consisting of halogen, $-CH_2F$, $-CHF_2$ and $-CF_3$.

2. A compound of claim 1 wherein Y is $-CF_3$.

3. A compound of claim 1 which is 2,6-bis(trifluoromethyl)-benzyl [1R, (1α, 3α)] 2,2-dimethyl-3-[(Z) 2-chloro-3,3,3-trifluoro-1-propenyl]]-cyclopropane carboxylate.

4. A method of combatting insects comprising contacting insects with an insecticidally effective amount of a compound of claim 1.

5. The method of claim 4 wherein the active compound is 2,6-bis(trifluoromethyl)-benzyl [1R, (1α, 3α)] 2,2-dimethyl-3-[(Z)-chloro-3,3,3-trifluoro-1-propenyl]]-cyclopropane carboxylate.

* * * * *